(12) United States Patent
Lambert

(10) Patent No.: US 12,280,237 B2
(45) Date of Patent: Apr. 22, 2025

(54) VARIABLE FLOW CONTROL DEVICE, SYSTEM AND METHOD

(71) Applicant: BIO HEALTH FRONTIERS, INC., El Dorado Hills, CA (US)

(72) Inventor: Paul Lambert, El Dorado Hills, CA (US)

(73) Assignee: BIO HEALTH FRONTIERS, INC., El Dorado Hills, CA (US)

( * ) Notice: Subject to any disclaimer, the term of this patent is extended or adjusted under 35 U.S.C. 154(b) by 325 days.

(21) Appl. No.: 17/879,702

(22) Filed: Aug. 2, 2022

(65) Prior Publication Data

US 2022/0370707 A1 Nov. 24, 2022

Related U.S. Application Data

(60) Continuation of application No. 16/933,946, filed on Jul. 20, 2020, now Pat. No. 11,433,179, which is a division of application No. 15/709,759, filed on Sep. 20, 2017, now Pat. No. 10,716,889, which is a continuation of application No. 15/397,153, filed on Jan. 3, 2017, now abandoned, which is a continuation of application No. 13/690,702, filed on Nov. 30, 2012, now abandoned.

(60) Provisional application No. 61/565,120, filed on Nov. 30, 2011.

(51) Int. Cl.
*A61M 5/168* (2006.01)
*A61M 5/142* (2006.01)
*A61M 39/10* (2006.01)

(52) U.S. Cl.
CPC ........ *A61M 5/142* (2013.01); *A61M 5/16813* (2013.01); *A61M 5/16881* (2013.01); *A61M 39/10* (2013.01)

(58) Field of Classification Search
CPC .............. A61M 5/142; A61M 5/16813; A61M 5/16881; A61M 5/16804; A61M 5/16877; A61M 5/16886
See application file for complete search history.

(56) References Cited

U.S. PATENT DOCUMENTS 4,769,008 A * 9/1988 Hessel ................... A61M 5/152 222/211
5,009,251 A * 4/1991 Pike ................... F16K 31/52416 137/561 A
5,234,413 A * 8/1993 Wonder ............ A61M 5/16881 604/246

* cited by examiner

*Primary Examiner* — Deanna K Hall
(74) *Attorney, Agent, or Firm* — Jones Day (57) ABSTRACT

A device, system and method are provided for controlling the rate of infusion of fluids during infusion therapy using non-electric infusion devices. Rotation of a flow regulator dial causes an orifice connected to the inlet to modify its position relative to a particular one or more orifices or groove portions, the characteristics of which provide a certain flow rate characteristic. The flow regulator allows for the infusion pump to infuse at a rate that may be varied during use by the user. Additionally, the flow regulator is made from a material selected to operate under a wide range of pressures, from 5-40 PSI, making the flow regulator compatible with pressurized devices, such as, a non-electric pump.

18 Claims, 8 Drawing Sheets

VARIABLE FLOW CONTROL DEVICE, SYSTEM AND METHOD

CROSS-REFERENCE TO RELATED APPLICATIONS

This application is a continuation of U.S. patent application Ser. No. 16/933,946 filed on Jul. 20, 2020 which, in turn, is a divisional of U.S. patent application Ser. No. 15/709,759, filed Sep. 20, 2017; which is a continuation of U.S. patent application Ser. No. 15/397,153, filed Jan. 3, 2017; which is a continuation of U.S. patent application Ser. No. 13/690,702, filed Nov. 30, 2012, which claims the benefit of U.S. Patent Provisional Application No. 61/565,120, filed Nov. 30, 2011; the contents of each of these applications are incorporated herein by reference in their entirety.

BACKGROUND OF THE INVENTION

Field of the Invention

The present invention relates to a device, system and method useful in infusion therapy, and more particularly, useful for varying the flow rate during infusion therapy.

Description of the Related Art

Infusion therapy requires the use of an infusion device (a source of positive pressure). There are several types of infusion devices which include: mechanical pumps, elastomeric pumps, gravity flow, electric/electronic pumps among others. Non-electric pumps and gravity infusions have a general disadvantage in that they often do not provide a sufficiently stable flow rate.

Flow rate control in mechanical, elastomeric and other non-electrical pumps is generally accomplished with the use of certain small diameter tubing (rate set) that regulates the flow. This presents the following limitations:

The flow cannot be adjusted during the infusion. Instead a new infusion set has to be used when a different rate is required. This adds cost and it may increase the risk of contamination.

In order to change the flow rate, the tubing diameter has to change and thus multiple rate sets have to be made available and changed during infusion. This may or may not be possible during certain therapies.

The nominal flow rate of these sets does not correspond to the flow rate during use due to the viscosity of the fluid often leading to patient and clinician confusion and errors.

Flow rate control in gravity infusions is generally accomplished with roller clamps or flow regulators that allow clinicians to determine a certain position to obtain a desired flow rate. Roller clamps are imprecise and they have generally no flow rate markings. Flow regulators in the prior art offer limited accuracy, versatility and pressure rating performance.

A clinician using flow regulators is generally unaware of the various factors that affect the performance of flow regulators including, the imprecise position of the flow regulator, relative temperature, relative humidity, patient backpressure factors, and the variability of pressure from the source of the medication. These factors can result in significant variances in flow rates and could adversely affect patients to a significant extent.

Flow rate controllers are generally labeled in ml/hour without taking into account the specific effect of the viscosity of the fluid which has a significant effect on the flow rate thus invalidating the significance of the markings of the device and confusing the clinician.

Safety concerns regarding infusions have been escalating in hospitals and in regulatory circles. The FDA has started presenting new guidance documents that regulate infusion system submissions to increase the threshold of requirements for such infusion systems.

Additional design requirements are becoming more apparent in Europe, Canada, Japan, the US and many other countries relative to improved control of flow rates and specific material biocompatibility regulations for fluid delivery devices.

Non-electric infusions systems are generally controlled by certain small diameter tubing (rate set) that regulates the flow. This method presents limitations including inability to change flow rate without changing the rate set, incorrect flow rate labeling due to the varying viscosities of fluids administered, and undesired flow rates due to device design limitations, patient and environmental factors. U.S. Pat. No. 4,904,239 ("the '239 patent") to Winchell et al., discloses an infusor having a distal flow regulator for dispensing a liquid under pressure at a predetermined flow rate. The '239 patent discloses the use of a non-adjustable, preselected flow regulator including a capillary bore. Col. 5 of the '239 patent, lines 9-14, disclose that a seal design permits the use of dramatically different length regulators for different desired flow rates, while still using the same size housing and connecting means, i.e., the preselected flow rate of the infusor can be changed simply by changing the length of the flow regulator. Thus, a particular flow regulator of the '239 patent has limited flow control characteristics.

U.S. Pat. No. 5,009,251 ("the '251 patent") to Pike et al., discloses a variable fluid flow controller for regulating the rate of flow from a source of fluid under pressure, including a plurality of unique flow restriction passageways, a valve associated with each passageway and a rotatable cam for selectively opening any one of the valves while maintaining the remaining valves closed. The flow restriction passageway of the '251 patent preferably comprises a channel etched on the surface of a first silicon wafer and enclosed by a second wafer to form a fluid flow passageway, one of the first or second wafers having a plurality of apertures therethrough for intersecting the passageway at various distances along its length.

U.S. Pat. No. 5,234,413 ("the '413 patent") to Wonder et al., discloses an infusion rate regulating device for varying the rate of flow of fluids for infusion to a patient at extremely low, but constant, flow rates. The regulator of the '413 patent is interposed at a point on a supply tube between a fluid reservoir and a patient. An input port directs fluid to a fluid metering groove of variable cross-sectional area on a metering plate which is formed as a part of the output port. The metering plate is rotated axially, relative to the input port, allowing fluid to enter the fluid metering groove at any point and flow toward the output port through a fluid metering groove which increases in depth or cross-sectional area at an essentially constant rate. Depending on the point at which the fluid enters the fluid metering groove flow path of the device in the '413 patent, the flow rate selected can be any rate from full off to full flow. Typically elastomeric devices operate in ranges under 5 psi.

What is needed is a flow control device for a gravity flow or mechanical infusion system that provides clinicians with precision in controlling the flow rate through the device for ranges of pressure higher than conventional elastomeric devices.

SUMMARY OF THE INVENTION

A device, system and method are provided for controlling the rate of infusion of fluids during infusion therapy using non-electric infusion devices. The flow control device of the present invention improves flow control, as well as safety resulting from such improved flow rate control, when compared to the performance of flow regulator devices in the prior art. The flow control device of the present invention has a design and method of construction that optimizes flow rate and functionality, safety and ergonomics in applications such as those that can be used with non-electric pumps including, but not limited to: mechanical pumps, elastomeric pumps, and other similar devices or applications.

An embodiment of the disclosure is a flow rate control device configured for connection in a flow path between a non-electric infusion pump and a patient, the flow rate control device comprising: an inlet handle; an outlet handle; a fluid path disposed between said inlet handle and said outlet handle, said fluid path having manually adjustable dimensions; and said inlet handle and said outlet handle composed of materials that can withstand pressures of from 5 PSI-40 PSI. In an embodiment, the flow rate control device further comprises a plurality of differently sized orifices for fluid flow therethrough located on at least one of said inlet handle or said outlet handle. In an embodiment, the flow rate control device further comprises a seal sealingly engaged between said inlet handle and said outlet handle.

An embodiment of the disclosure is a variable flow rate infusion system, comprising: a non-electric infusion pump that dispenses fluid pressurized to between 5 PSI and 40 PSI; and a flow control device according to claim 1 in fluid communication with said non-electric infusion pump. In an embodiment, said materials include at least one of polycarbonate and another material having a similar hardness coefficient to polycarbonate.

In one particular embodiment of the invention, a variable flow control device is provide in which the rotation of a flow regulator dial causes an orifice connected to the inlet to modify its relative position with respect to a groove or open-topped channel connected to the fluid outlet, via an orifice at one end of the groove, thus defining the fluid path. In this embodiment, one or more characteristics (diameter, width, depth, etc.) of the groove may be varied along the length of the groove, as desired.

In another particular embodiment of the invention, rotation of a regulator dial causes an orifice connected to the inlet to align with one of a plurality of orifices connected to the outlet. The diameter of each orifice of the plurality may be graduated such that the different orifices represent a percentage of flow from 1% to 100% in specific increments. In one particular embodiment, ten orifices are provided each orifice providing a 10% greater flow rate of the total possible flow rate than its immediately prior neighbor, starting from the smallest orifice to the largest, with the first orifice providing 10% of the total possible flow rate and the tenth orifice providing 100% of the total possible flow rate.

In a further particular embodiment of the invention, rotation of a flow regulator dial causes an orifice connected to the inlet to align with one of various combinations of orifices connected to the outlet that represent the permutation of orifices as a digital counter (BINARY).

Additionally, in a further particular embodiment of the invention, improved flow regulation or control is achieved by combining two or more adjustable dial layers, each having a variable flow control mechanism in accordance with the present invention. In one particular embodiment, one or more additional variable flow control layers are added after the first or main variable flow control layer to provide a combination of coarse and fine control levels, thus greatly enhancing the actual flow rate controllability through the device.

The present invention solves important limitations inherent to non-electric infusion systems. Other features which are considered as characteristic for the invention are set forth in the drawings and the appended claim.

Although the invention is illustrated and described herein as embodied in a variable flow control device, system and method, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

For a fuller understanding of the nature of the present invention, reference should be made to the following detailed description, taken in connection with the accompanying drawings in which like reference numerals refer to like elements and in which.

DETAILED DESCRIPTION OF THE PREFERRED EMBODIMENT

Figure 19:
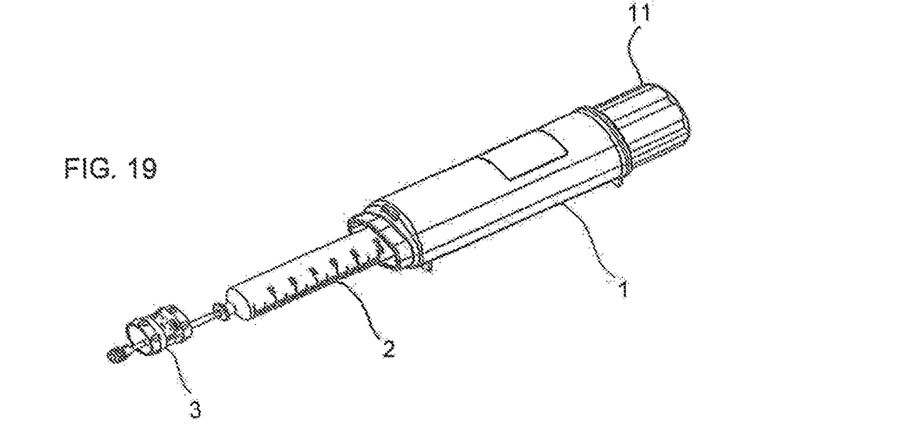
FIG. 19 is a perspective view of an infusion system with a pump, a syringe and a flow regulator in accordance with one particular embodiment of the present invention.

Referring now to FIGS. 1-6B, there is shown a variable flow control device 100 in accordance with one particular embodiment of the present invention. The flow control device 100 optimizes the delivery of fluids in conjunction with non-electric infusion pumps and gravity flow, so as to control the infusion of fluids for infusion therapy administration without the use of electronic infusion devices. The flow control device 100 is a variable flow regulator that can be provided as part of a complete infusion system or set. One example of one such complete infusion system or set is illustrated in FIG. 19.

Figure 1:
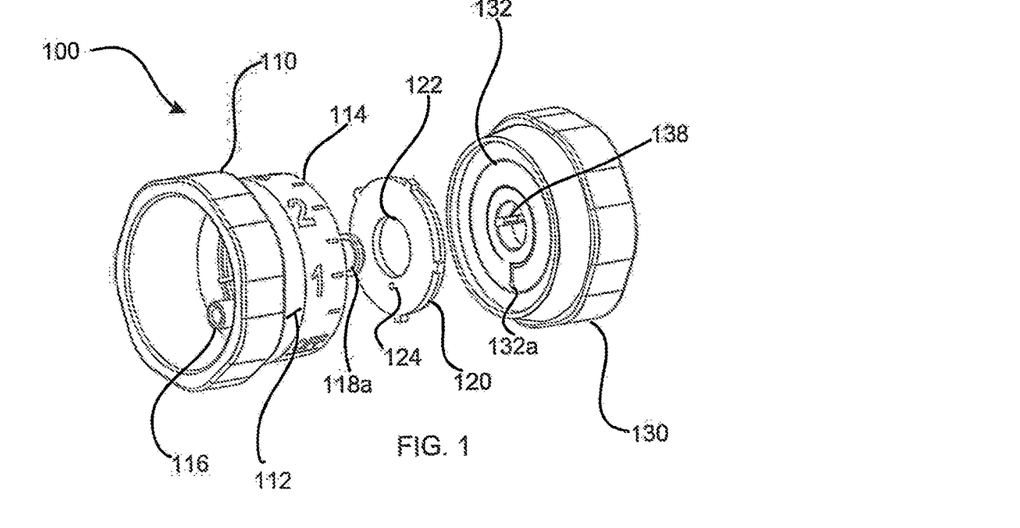
FIG. 1 is an exploded, perspective view of a flow control device in accordance with one particular embodiment of the invention.
Figure 2:
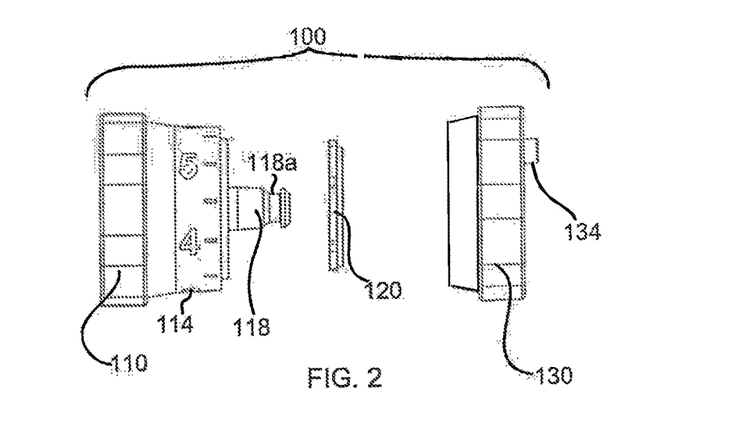
FIG. 2 is an exploded view, taken from the side, of the flow control device of FIG. 1.
Figure 3:
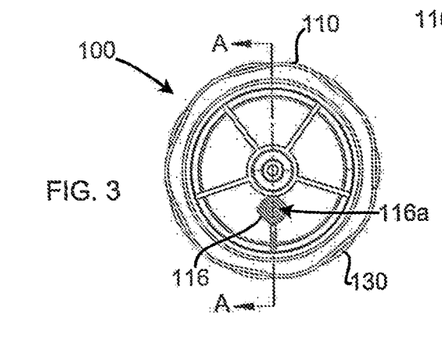
FIG. 3 is a top plan view of a flow control device in accordance with one particular embodiment of the invention.
Figure 3A:
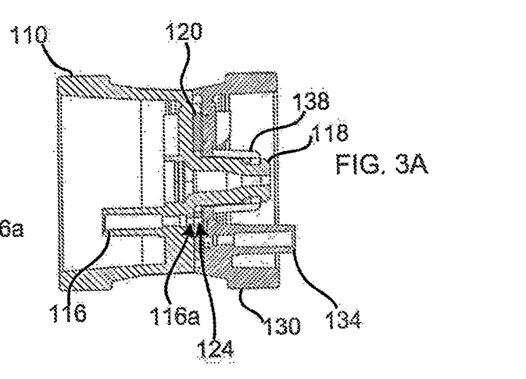
FIG. 3A is a cut-away view of the flow control device of FIG. 3, taken along the section lines A-A.
Figure 4A:
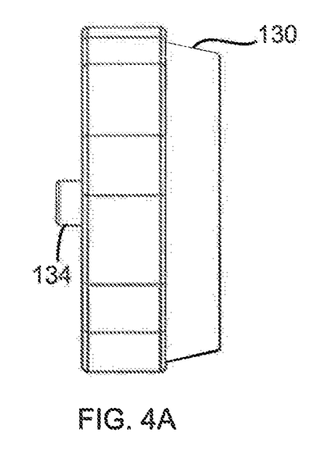
FIG. 4A is a side plan view of a portion of a flow control device in accordance with one particular embodiment of the invention.
Figure 4B:
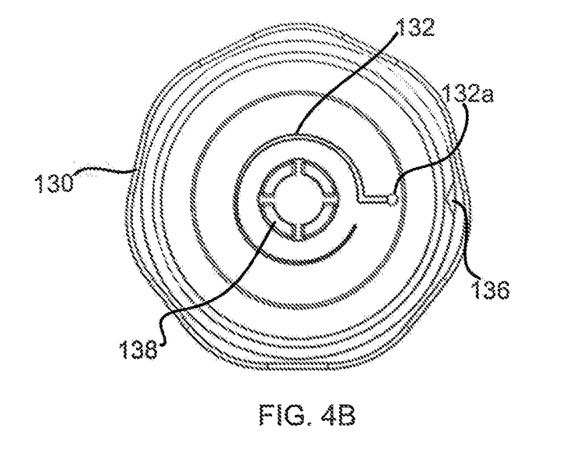
FIG. 4B is a top plan view of the portion of the flow control device of FIG. 4A.
Figure 5A:
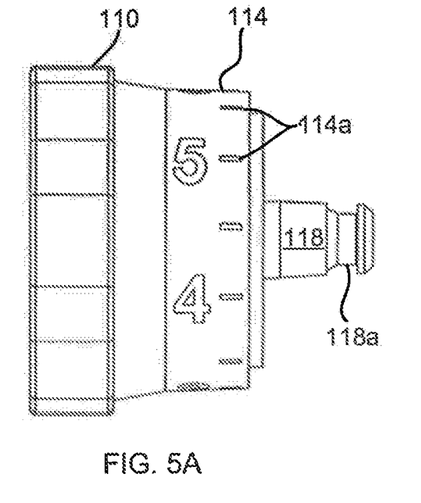
FIG. 5A is a side plan view of a portion of a flow control device in accordance with one particular embodiment of the invention.
Figure 5B:
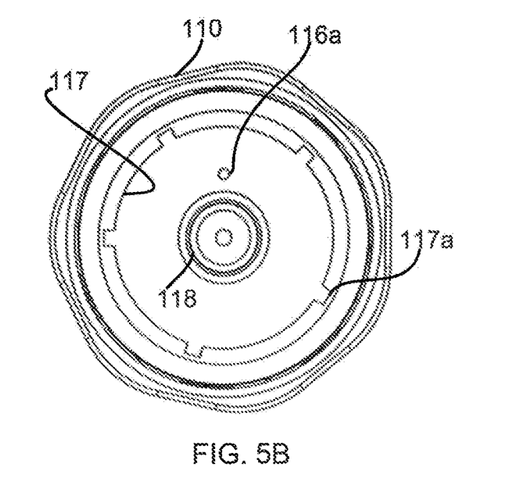
FIG. 5B is a top plan view of the portion of the flow control device of FIG. 5A.
Figure 6A:
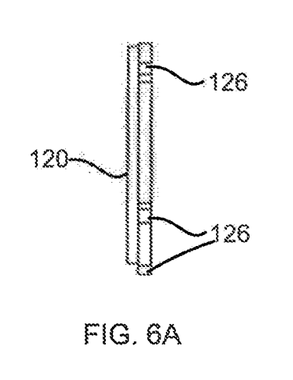
FIG. 6A is a side plan view of a portion of a flow control device in accordance with one particular embodiment of the invention.
Figure 6B:
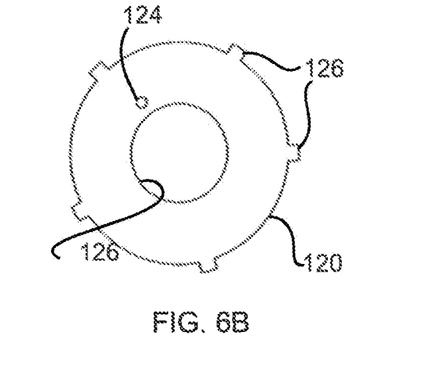
FIG. 6B is a top plan view of the portion of the flow control device of FIG. 6A.

In the present preferred embodiment, the flow control device 100 of the present invention is constructed with biocompatible materials. Preferably, flow control device 100 is designed with a geometry that is conducive to hand manipulation with sufficient gripping areas to avoid slippage and to facilitate rotation as a way to select a specific flow rate. The flow control device 100 is made with materials that allow for the infusion apparatus to be operated under gravity, as well as, pressurized at higher pressure ranges, such as from 5 PSI-40 PSI, as required by elastomeric and mechanical infusion devices designed to deliver fluids that require pressurized chambers in the 5-40 PSI range. The main flow rate variation is accomplished by adjusting the fluid path dimensions. Rotation of one half of the flow regulator component in one direction moves the fluid path exit point along the channel and effectively changes total fluid path length and diameter such that fluid flow decreases or stops depending on the degree to which it is rotated. Rotation in the opposite direction moves the fluid path exit point towards the upstream fluid path entry point, changing effective internal fluid path length and diameter such that flow is increased.

The flow control device 100 includes three primary elements: an inlet handle 110; an outlet handle 130; and a seal 120, enclosed (i.e., "sandwiched" or sealingly engaged) between the inlet handle 110 and the outlet handle 130. The outer surface of the inlet handle 110 includes a circumferential face or viewing portion 112 upon which a scale 114 showing selectable flow rates is imprinted. In the present embodiment, the inlet handle 110 and scale 114 provide a flow regulator dial that is rotatable relative to the outlet handle 130 to control the fluid flow through the device 100.

The inlet handle 110 includes a port 116 which serves as the fluid inlet to the device 100. The port 116 includes a distal orifice 116a that allows fluid input to the port 116 to flow to the rest of the device 100. The inlet handle 110 additionally includes a shaft 118 that includes a collar portion 118a that engages a snap fitting 138 of the outlet handle 130 to form a rotatable snap-fit coupling which holds the seal 120 in place between the inlet handle 110 and the outlet handle 130. More particularly, the shaft 118 passes through a central hole 122 in the seal 120 and is entrapped in the snap fitting 138 of the outlet handle 130, by its collar 118a.

The outlet handle 130 includes an internal groove or "channel" 132 open at the top and of varying diameter, through which fluid passes to an orifice 132a at one end of the groove 132 connected to an outlet port 134. The relative positions (i.e., overlap) of the inlet handle orifice 116a and the outlet handle groove 132 determines the flow rate. The outlet port 134 of the outlet handle 130 permits fluid to flow from the device 100 to tubing connected to a connector, preferably some form of universal connector, to allow connection to a patient.

During assembly, the seal 120 is seated into an area of similar geometry to the seal 120 in the order to maintain the hole or orifice 124 through the seal 120 in alignment with the inlet handle orifice 116a. For example, as can be seen more particularly from FIGS. 5B and 6B, the lower portion of the inlet handle 110 includes a chamber or cavity 117, sized and shaped to receive the seal 120 without permitting slippage. For example, the projections 126 on the seal 120 fit into mating recesses 117a in the cavity 117 to prevent the seal 120 from moving in the cavity 117, and thus maintaining the orifice 116a in direct alignment with the orifice 124, as shown more particularly in FIG. 3A. This alignment permits fluid from the inlet handle 110 to flow through the seal 120 and into the groove 132 of the outlet handle. The seal orifice 124 is aligned with the orifice 116a and groove 132, both during assembly and during flow. The seal 120 ensures that fluid is contained within the groove 132, and that fluid input to the device 100 via the port 116 can only flow in a path defined by the orifices in each of the inlet handle 110 and seal 120 and groove 132 of the outlet handle 130, to exit the device 100 through the port 134 of the outlet handle 130.

The inlet handle 110 and outlet handle 130 are preferably made of a material sufficiently robust to withstand the pressures of the intended use. In one particular embodiment of the invention, it is intended that the device 100 be used in a pressurized infusion system. Consequently, the material selected for inlet handle 110 and outlet handle 130 is preferably selected to operate under a wide range of pressures from 5-40 PSI (i.e., the device being operable for the entire range), making the device 100 compatible with pressurized devices. In one particular preferred embodiment, the material for the inlet and outlet handles 110, 130 are selected to be polycarbonate or other materials of similar hardness coefficient. For example, the inlet and outlet handles can be made of a hard plastic to ensure precise sealing. The seal 120 is made of a soft plastic to provide a cushioned seal when placed between the inlet and outlet handles 110, 130 and seals the device to prevent fluid leakage. The tolerance of the molds to produce the inlet and outlet handles should take into account that the inlet and outlet handles should be of sufficient tightness to avoid fluid leakage.

Fluid viscosity, relative position of device, atmospheric pressure, ambient temperature and other factors affect actual flow rates. Calibration of flow rates and enhanced controllability are important clinical features. The flow control device of the present invention may be calibrated and delivered to the user with charts that correlate fluid viscosity with flow rate for various fluids under various conditions as part of the operating manual. The charts provided may include adjustment factors to account for and compensate for, among other factors that affect actual flow rates, fluid viscosity, relative position of device, atmospheric pressure, and/or ambient temperature and other factors.

Conventional flow regulators are rated in ml/hr (milliliters per hour) and based on gravity flow for a low viscosity "Saline solution". This way of labeling flow regulators is misleading and cannot be correlated to parametric variations. Instead, the device 100 has a numbering system that replaces the otherwise imprecise ml/hr indicators with numbers either from 1-6, 1-10 or 1-100% thus avoiding empirical discrepancies when different fluids are utilized. For example, in the present particular embodiment shown in FIGS. 1 and 2, the scale 114 on the device 100 is labeled 1-6, which in the present example are not a numerical value in ml/hr. Each number on the scale 114 is aligned with a hash mark 114a, and the scale 114 additionally includes intervening hash marks 114a disposed halfway between the numbers, which hash marks 114 are alignable with an indicator or arrow 136 on the outlet handle 130, for easy and understandable selection of the flow. More particularly, the inlet handle 110 and gasket or seal 120, with the aligned orifices, 116a, 124, rotate relative to the groove 132 of the outlet handle 130, to align the orifices 116a, 124 with different portions of the groove 132, thus controlling the flow between the inlet port 116 and the outlet port 134.

Referring now to FIGS. 7-12B, there is shown a variable flow control device 200 in accordance with another particular embodiment of the present invention. The flow control device 200 is similar in many respects to that of FIGS. 1-6B. More particularly, the flow control device 200 includes an inlet handle 210 including an inlet port 216, orifice 216a, scale 214, chamber or cavity 217 and shaft 218, all of which operate similarly to the correspondingly named parts described in connection with FIGS. 1-6B. The flow control device 200 additionally includes a seal 220 and an outlet handle 230. However, instead of a single orifice, the seal 210 includes a plurality of orifices 222 alignable between the orifice 216a of the inlet handle 210 and a channel 236 containing an outlet orifice 232 connected to the outlet port 234 of the outlet handle 230.

Figure 7:
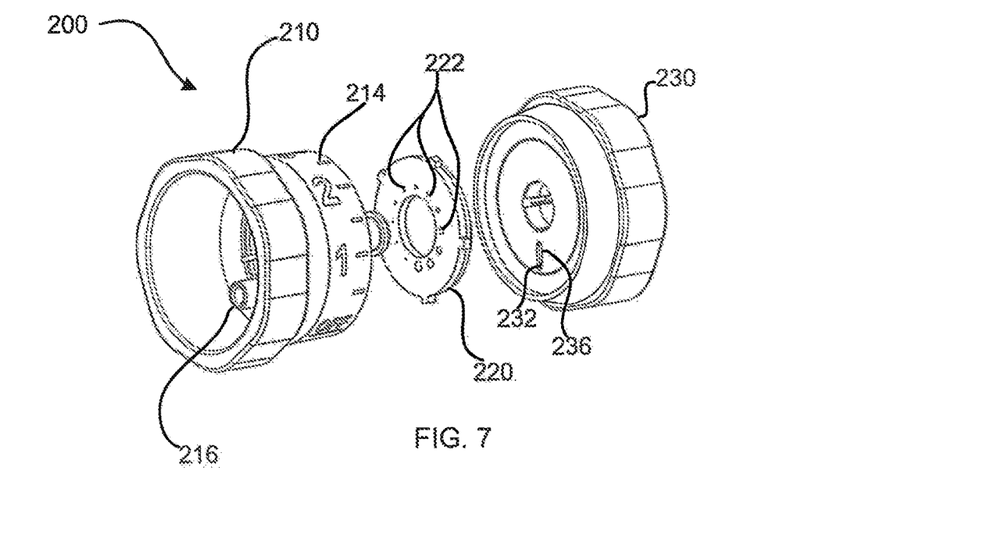
FIG. 7 is an exploded, perspective view of a flow control device in accordance with another particular embodiment of the invention.

However, the scale on the outlet handle 210 is mounted, in the present embodiment, on a dial 214 that can be rotated relative to the body of the inlet handle 210. The chamber 217 containing the seal 220 forms the base of the dial 214, so that, when received in the chamber 217, the seal 220 is rotated when the dial 214 is rotated. Rotation of the dial 214 to a discretely marked position will align one of the orifices 222 (or no orifice, in the case of the "OFF" setting) with the inlet orifice 216a and with the channel 236 of the outlet handle 230. The channel 236 is sized to receive fluid from any of the holes 222 and channel it to the outlet orifice 232 at the base of the channel 236.

In one particular embodiment of the invention, the scale on the dial 214 is operable between Off and 10 and the seal 220 includes 10 orifices 222. Rotation of the dial 214 relative to the arrow or indicator 235 on the outlet handle 230 places a different orifice 222 between the inlet orifice 216a and the channel 236 containing the outlet orifice 232. Each of the different orifices 222 are differently sized from one another to provide a correspondingly different flow through the seal 220, and thus out the outlet port 234. In the present example each orifice 222 is sized to provide a percentage of flow through the seal 220. In the example shown, each of the 10 markings on the scale of the dial 214 represents 10% of the flow, such that aligning the number 1 on the dial 214 with the arrow 235 aligns an orifice 222 that permits fluid to flow at a flow rate of 10% of the total possible flow rate, between the inlet orifice 216a and the outlet orifice 232. Similarly, selecting the hash mark next to the number 2 represents 20% of the total possible flow rate, while selecting the hash mark next to the number 10 represents 100% of the total possible flow rate. Although the present example uses 10 discrete orifices 222 to provide flow rates changeable at 10% increments, this is not meant to be limiting, as more or fewer orifices 222 can be used. For example, if desired, 100 orifices 222 can be provided to permit the selection of a flow rate between 0 and 100% in 1% increments. Other numbers of orifices 222 can be used without deviating from the spirit of the invention.

Figure 8:
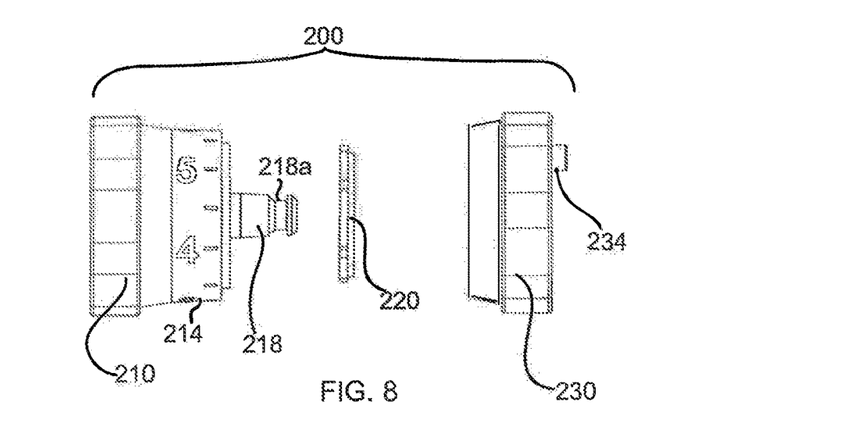
FIG. 8 is an exploded view, taken from the side, of the flow control device of FIG. 7.
Figure 9:
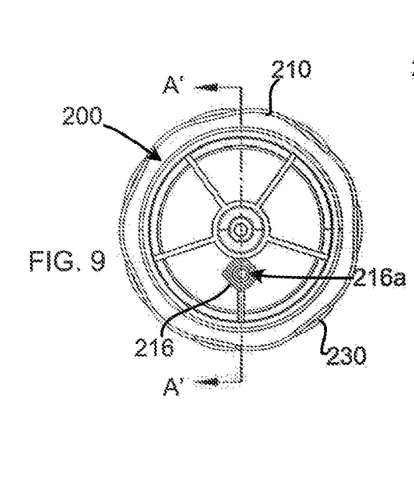
FIG. 9 is a top plan view of a flow control device in accordance with one particular embodiment of the invention.
Figure 9A:
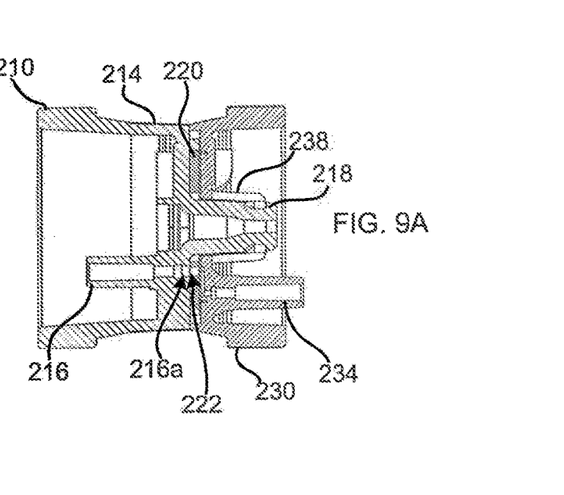
FIG. 9A is a cut-away view of the flow control device of FIG. 9, taken along the section lines A'-A'.
Figure 10A:
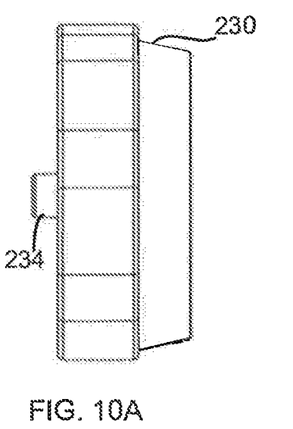
FIG. 10A is a side plan view of a portion of a flow control device in accordance with one particular embodiment of the invention.
Figure 10B:
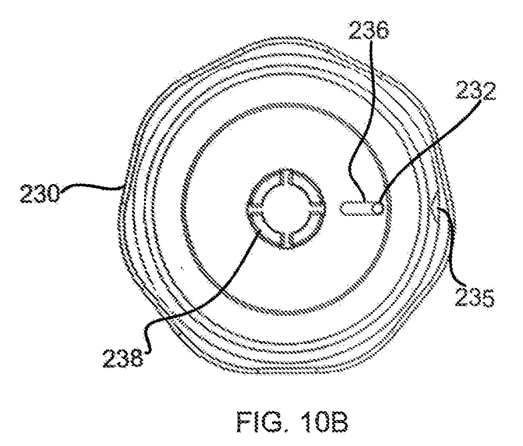
FIG. 10B is a top plan view of the portion of the flow control device of FIG. 10A.
Figure 11A:
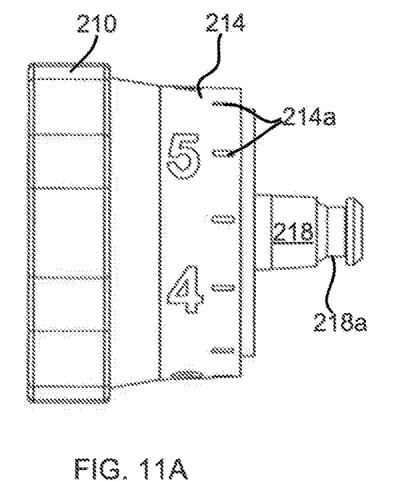
FIG. 11A is a side plan view of a portion of a flow control device in accordance with one particular embodiment of the invention.
Figure 11B:
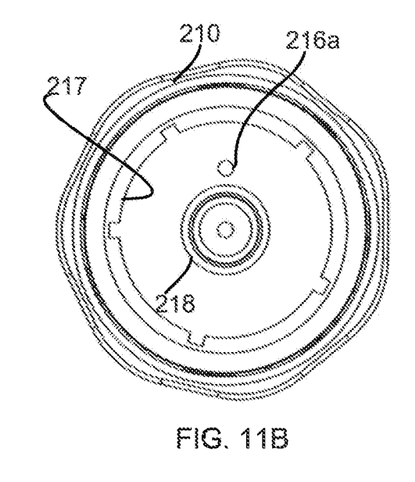
FIG. 11B is a top plan view of the portion of the flow control device of FIG. 11A.
Figure 12A:
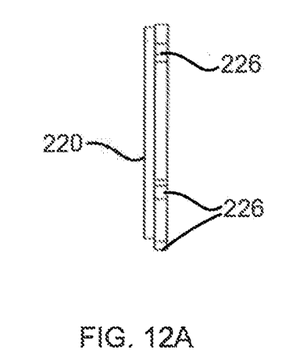
FIG. 12A is a side plan view of a portion of a flow control device in accordance with one particular embodiment of the invention.
Figure 12B:
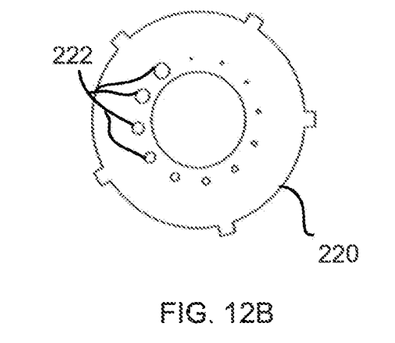
FIG. 12B is a top plan view of the portion of the flow control device of FIG. 12A.

Additionally, the flow control device 200 is preferably made of the same materials, and for operation in the same pressure range, as the device 100, described above. Additionally, the device 200 is assembled using a snap-fit coupling between a shaft 218, having a collar 218a, and a snap fitting 238 on the outlet handle 230, with the seal 220 disposed there between.

Figure 13:
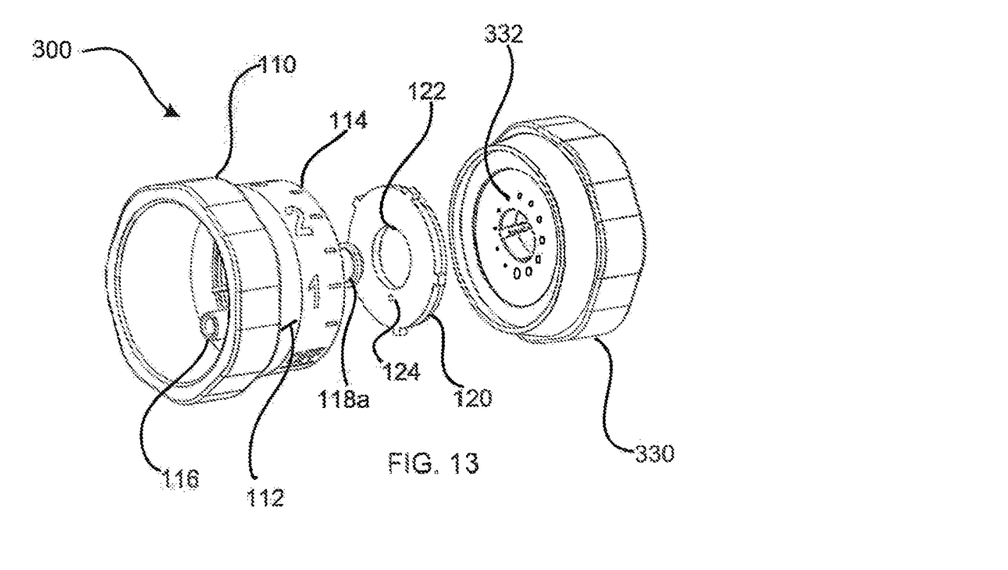
FIG. 13 is an exploded, perspective view of a flow control device in accordance with a further particular embodiment of the invention.
Figure 14:
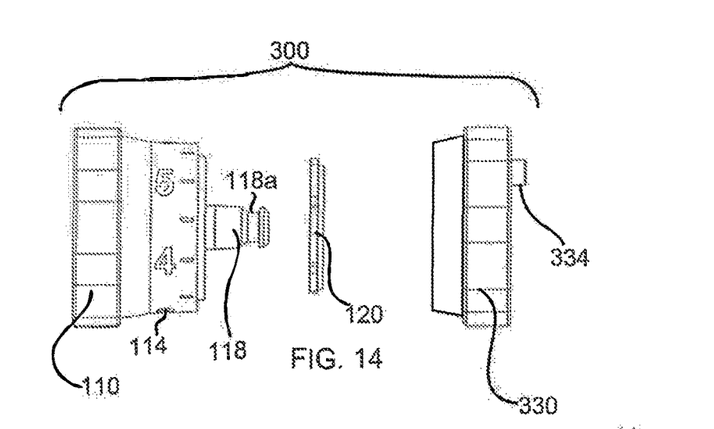
FIG. 14 is an exploded view, taken from the side, of the flow control device of FIG. 13.

Alternately, if desired, instead of a plurality of orifices 222 being provided on the seal 220, the plurality of orifices can be provided on a face of the outlet handle, as shown more particularly in the embodiment of FIGS. 13 and 14. Referring more particularly to FIGS. 13 and 14, the seal can be the seal 120, as described in connection with the embodiment of FIG. 1. Similarly, the inlet handle can be the inlet handle 110 described in connection with the embodiment of FIG. 1. Thus, the combination of inlet handle 110 and seal 120 would operate as described in connection with FIG. 1 (i.e., with the single orifice of the seal 120 fixedly aligned with the orifice 116a of the inlet handle 110). However, instead of the outlet handle 130, the device 300 includes the outlet handle 330, the face of which includes a plurality of orifices 332, each of a different size, as described in connection with the orifices 222 of FIG. 7. The outlet handle 330 contains various internal "channels" connecting the orifices 332 to the outlet port 334, through which the fluid travels. Rotation of the inlet handle 110 relative to the outlet handle 330 provides fluid from the inlet port 116, via the orifices 116a (see, for example, FIG. 3A) and 124, to an aligned one of the orifices 332. The diameter of the aligned one of the orifices 332 and/or the channel connecting it to the port 334, define the rate of flow.

As with the other embodiments, the numbers on the scale 114 can be aligned with the arrow or indicator to align the orifices 116a, 124 with a particular desired orifice 332 and provide the fluid to the outlet port 334 at the rate defined by the particular respective orifice 332.

Referring now to FIGS. 15-18, there is shown a flow control device 400 in accordance with a further embodiment of the present invention. The device 400 includes an inlet handle 410 having a rotating dial 414, an outlet handle 430 and a seal 420 including specialized groupings of orifices 422 defined for each possible discrete setting for the dial 414. The flow control device 400, i.e., the elements 410, 420 and 430, is preferably made of the same materials, and for operation in the same pressure range, as the corresponding elements of the device 100, described above. Additionally, the device 400 is assembled using a snap-fit coupling between a shaft and snap fitting, with the seal 420 disposed therebetween, as was described in connection with the previous embodiments.

Additionally, in the present embodiment, the rotation of the flow regulator dial 414 causes the flow from the inlet orifice or port 416 to be connected to the outlet handle 430, via a particular group of orifices 422 in the seal 420. More particularly, the seal 420 includes fifteen discrete positions, each of which has a unique group or combination 422 of orifices representing a specific binary number. In the present example, the inlet orifice 416a may be a single orifice, as shown, which is large enough to feed fluid to all of the orifices 422a in a particular group 422. Alternately, if desired, the inlet 416 can be configured to have four orifices 416a, one for alignment with each of the four possible orifice locations in a group 422 on the seal 420. Additionally, if desired, the orifice 416a can be in the form of a slot or groove (such as the groove 436 on the outlet handle), to ensure that fluid from the inlet port 216 will be provided to any open orifice in a group of orifices 422. The number of orifices open between the inlet orifice 416a, and the outlet slot 436 and orifice 432, as well as their sizes, define the flow rate for each particular position or setting of the dial 414. As can be seen, with the use of four possible orifices 422a per group 422, there are fifteen possible flow rate settings available to the flow rate device 400, as shown in Table 1, here below.

TABLE 1

Figures 15, 16, 18:
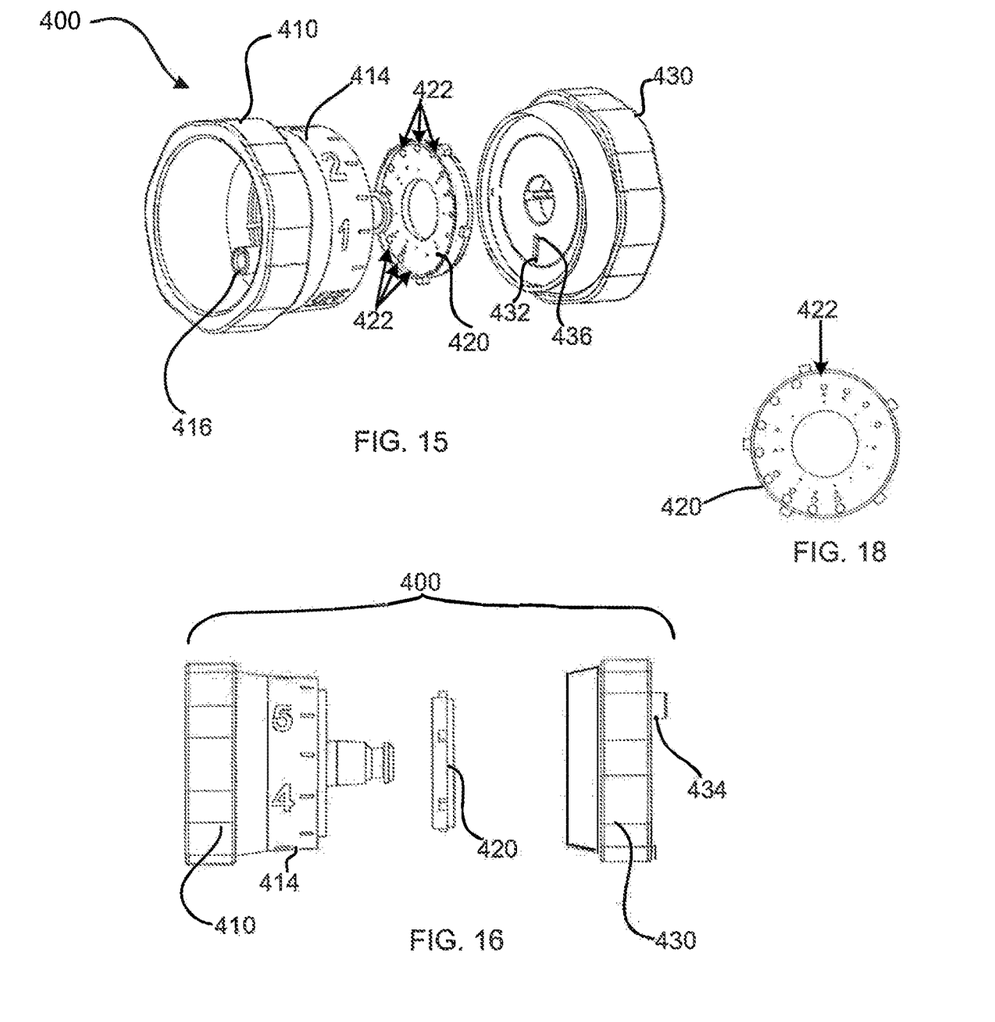
FIG. 15 is an exploded, perspective view of a flow control device in accordance with still another particular embodiment of the invention.
FIG. 16 is an exploded view, taken from the side, of the flow control device of FIG. 15.
FIG. 18 is a top plan view of the portion of the flow control device in accordance with one particular embodiment of the invention.
Figure 17:
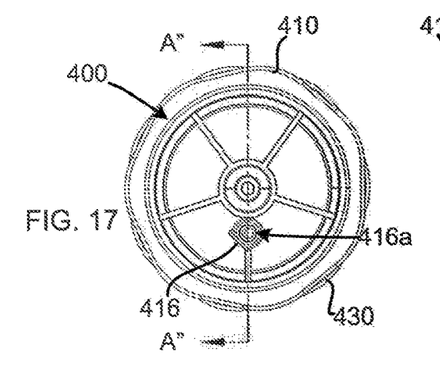
FIG. 17 is a top plan view of a flow control device in accordance with one particular embodiment of the invention.
Figure 17A:
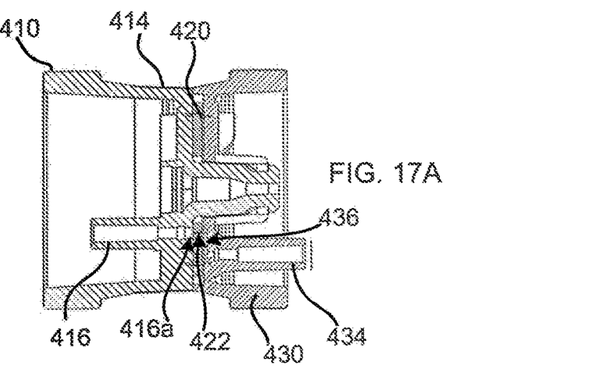
FIG. 17A is a cut-away view of the flow control device of FIG. 17, taken along the section lines A"-A"

| | ORIFICE | | | |
|---|---|---|---|---|
| POSITION No. | ONE | TWO | THREE | FOUR |
| 1 | 1 | 0 | 0 | 0 |
| 2 | 0 | 1 | 0 | 0 |
| 3 | 1 | 1 | 0 | 0 |
| 4 | 0 | 0 | 1 | 0 |
| 5 | 1 | 0 | 1 | 0 |
| 6 | 0 | 1 | 1 | 0 |
| 7 | 1 | 1 | 1 | 0 |
| 8 | 0 | 0 | 0 | 1 |
| 9 | 1 | 0 | 0 | 1 |
| 10 | 0 | 1 | 0 | 1 |

TABLE 1-continued

| | ORIFICE | | | |
|---|---|---|---|---|
| POSITION No. | ONE | TWO | THREE | FOUR |
| 11 | 1 | 1 | 0 | 1 |
| 12 | 0 | 0 | 1 | 1 |
| 13 | 1 | 0 | 1 | 1 |
| 14 | 0 | 1 | 1 | 1 |
| 15 | 1 | 1 | 1 | 1 |

As shown more particularly in FIG. 18, the size of each orifice 422a in a group 422 is, preferably, different from the size of every other orifice 422a in the group 422, which provides the high resolution of fifteen unique possible dial positions. Additionally, the size of the holes should gradually increase. For example, in order to effectuate the fifteen unique settings of Table 1, in the present illustrative example, the orifice 2 must be larger than (i.e., have a greater flow through) the orifice 1. Similarly, orifice 3 must be larger than orifices 1 and 2, combined, and orifice 4 must be larger than orifices 1, 2 and 3 combined. In one particular embodiment of the invention, the second orifice is double the flow rate of the first orifice, the third orifice is double the flow rate of the second orifice and the fourth orifice is double the flow rate of the third orifice, and so on for the total number of orifices used. Note that that use of four orifices per group is not meant to be limiting, as more or fewer orifices 422a per group 422 may be used without departing from the scope of the invention. For example, in another particular embodiment of the invention (not shown), each group of orifices could have between 1 and 3 orifices, thus defining 8 unique flow rate settings, as defined by Table 2, herebelow.

TABLE 2

| | ORIFICE | | |
|---|---|---|---|
| POSITION No. | ONE | TWO | THREE |
| 1 | 1 | 0 | 0 |
| 2 | 0 | 1 | 0 |
| 3 | 1 | 1 | 0 |
| 4 | 0 | 0 | 1 |
| 5 | 1 | 0 | 1 |
| 6 | 0 | 1 | 1 |
| 7 | 0 | 1 | 1 |
| 8 | 1 | 1 | 1 |

Figure 24:
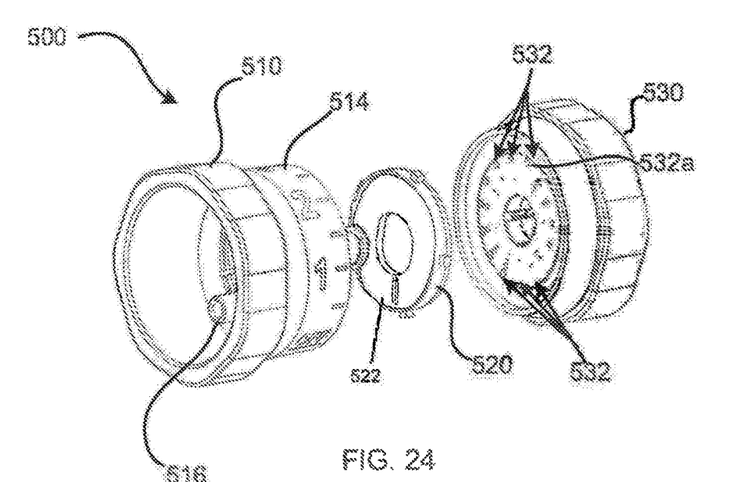
FIG. 24 is an exploded, perspective view of a flow control device in accordance with still another particular embodiment of the invention.

Additionally, if desired, in addition to, or instead of, the seal having groups of orifices, as described, the outlet handle, itself, may include a sequence of orifices, defined by Table 1, that permit fluid to flow through from seal into one such group of orifices. The relative position of the inlet handle and seal orifices with a particular group of orifices in the outlet handle determines the flow rate. One particular example of a flow rate device 500, wherein the orifice groups 532 are on the outlet handle, instead of on the seal, is shown in FIG. 24. More particularly, the inlet handle orifice is aligned with a slot 522 on the seal 520, which can be aligned with each linear orifice group of 532 on the outlet handle 530 by rotating the inlet handle 510 relative to the outlet handle to align with a setting marked on the dial 514. This changes the position of the slot 522 (and inlet orifice 516) relative to the surface of the outlet handle 530, and aligns the slot 522 with one of the particular orifice groups 532. Channels in the outlet handle 530 direct the fluid from each orifice 532a of a group 532 to the outlet port (Not shown) of the device 500.

Figure 20:
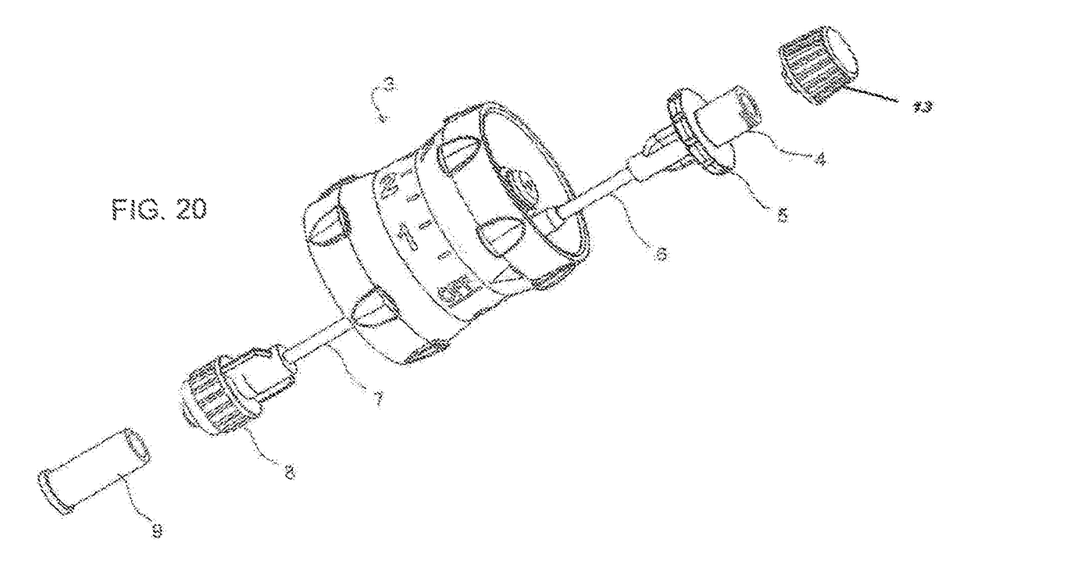
FIG. 20 is a perspective view of a flow regulator according to the invention and its connectors to the remainder of the infusion system.

Referring now to FIGS. 19-20, there is shown a pump 1 and a syringe 2 inserted in the pump 1. A flow regulator 3 according to the invention is connected to the syringe 2. The flow control device 3 can be any of the devices 100, 200, 300, 400 discussed hereinabove. The pump 1 is designed with a pressure rating that is higher than elastomeric devices. The syringe 2 is a conventional, commercially available syringe. The flow regulator is provided with the necessary tubing and with commercially available universal female and male luer lock connectors. The female luer lock 4 is connected to the source of infusion and the male luer lock 8 is connected to the patient via a catheter or an additional extension infusion set.

Figure 22:
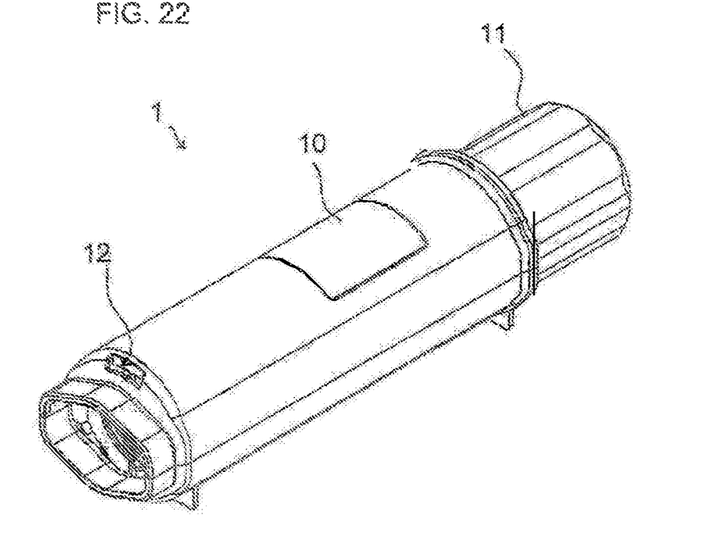
FIG. 22 is a perspective view of an infusion pump that can be used in an infusion system in accordance with one particular embodiment of the invention.

FIG. 22 shows the infusion pump 1 of FIG. 19 on a larger scale. The illustrated infusion pump 1 is the preferred embodiment in the context, but it will be understood that the flow regulator 3 according to the invention may also be used with other infusion pumps. The novel pump has label surface 10 for branding and the like. A rotating knob 11 or handle 11 may be used to initialize the pump. A viewing window 12 is provided for ascertaining that the syringe is properly inserted in the pump 1.

The following sequence may be performed by the user/patient in order to initialize the system and start the delivery of the infusion medicament:

First, the regulator 3 must be set to zero in order to block any flow there through. Then the luer lock connector is attached to the filled syringe 2.

Next, the needle set is connected to the luer lock on the regulator 3.

Then the pump drive is opened by rotating the handle 11 counterclockwise until it stops.

Then the syringe 2 is loaded and locked into the pump 2 by inserting the syringe plunger into the pump 1 and rotating the syringe 90° until it "clicks" in place.

Next, the user can verify that the syringe flange shows in the viewing window 12, so as to confirm that the syringe is properly loaded.

Now, the pump is ready for activation. It is activated by rotating the handle 11 clockwise.

The system is primed by turning the regulator dial to position 5, for instance, and, when the first drop of fluid comes out of the needle set, turning it back to the zero position.

Now the infusion can be started as prescribed by the health provider. The user should thereby refer to the flow control guide.

The delivery may be stopped by turning the regulator dial to the zero or off position.

The syringe may be removed after the regulator has been set to zero and the handle 11 is rotated counterclockwise until the stop is reached.

Figure 23:
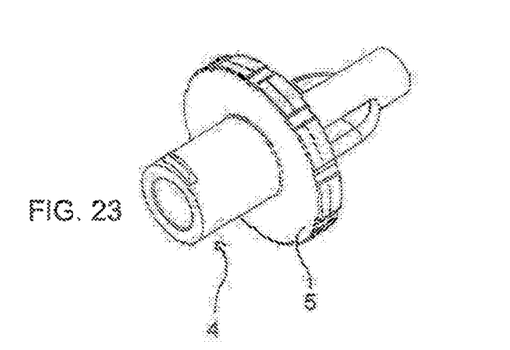
FIG. 23 is a perspective view of an exemplary luer lock for use in one particular embodiment of an infusion system in accordance with the present invention.

FIG. 23 is an enlarged view of a luer lock 4 for use in the novel infusion system. The luer lock is particularly easy to handle due to its ergonomic geometry.

The entire flow control device 3 and connection system is illustrated in FIG. 19. The female luer lock 4 is provided for conventional connection to the delivery end of the syringe 2. A removable cap 13 is provided so as to protect the luer lock 4 during shipping and storage. A tubing section 6 leads from the luer lock 4 to the inlet side of the flow regulator 3. The outlet side of the flow regulator 3 is connected via tubing 7 to a further connector 8 (here, a male luer lock), which is connected into the delivery IV tubing system 9.

The flow control device or regulator of the present invention is different from all other flow regulators in the market, in part, because all others are unable to withstand the considerable pressures supplied by the pump 1, or other pumps with similar pressure ratings. Additionally, the flow control device of the present invention provides greater resolution for more accurately controlling the rate of fluid flow.

As can be seen from the foregoing, flow control device 3 allows for the infusion pump to infuse a rate that is controllable by the user. Additional flow regulation control can be accomplished by incorporating one or more supplemental adjustable dial layers. For example, referring now to FIG. 21, there is shown another embodiment of a flow rate control device 20, wherein two dials 22, 24 are used to improve precision in controlling flow rate. The first layer (22, 30) provides a coarse control with methods described in connection with the foregoing embodiments discussed above. The second layer (24, 32) provides a fine control, again with methods described in the foregoing embodiments discussed above. This is not meant to be limiting, as additional layers may be provided without departing from the scope of the invention.

Figure 21:
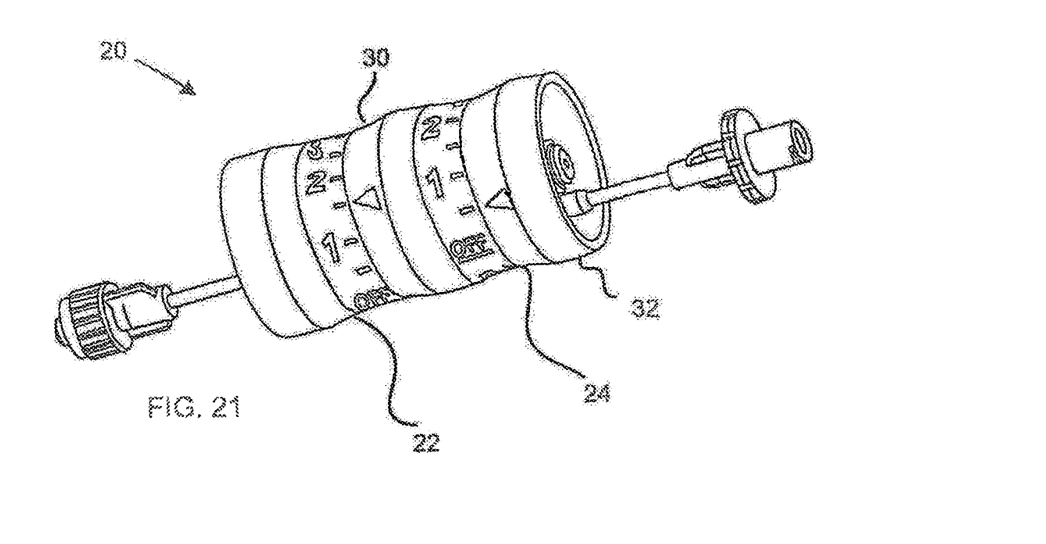
FIG. 21 is a perspective view of a flow control device in accordance with still another particular embodiment of the present invention.

More particularly, as shown in FIG. 21, the two layers are designed to provide a combination of coarse and fine control levels, thus greatly enhancing the actual flow rate controllability based on the selections/adjustments made on the first dial 22 and second dial 24. Each of the dials 22, 24 may work in accordance with the principles described herein. The second dial 24 may provide fine flow control, further refining the output controlled by the first dial 22, which provides coarse flow control. In one particular embodiment, the second dial has a base diameter ranging between 0-10% of the first dial, which has a diameter ranging between 0-100% (coarse flow control). The combination of the first and the second dials 22, 24 yields significantly enhanced control. Additional layers having a compounding effect on enhanced resolution, controllability and accuracy of the device 20 may be provided. Each layer may use the same or a different flow control mechanism as any other layer, as desired. For example, the coarse layer, including the dial 22 and outlet handle portion 30, can make use of a variable diameter groove for controlling flow, such as described in connection with the device 100 FIG. 1, while the second layer, including the dial 24 and the outlet handle portion 32 may make use of one of the other flow control mechanisms described in connection with the devices 200, 300, 400, 500. This is not meant to be limiting, as any combination of layers and any number of layers utilizing the variable flow control mechanisms described in connection with the devices 100, 200, 300, 400, 500 may be used in any of the layers without departing from the spirit of the present invention.

As can be seen from the foregoing, the present invention implements features that improve flow control as well as safety resulting from such improved flow rate control when compared to the performance of devices in the prior art. The invention solves important limitations inherent to non-electric infusion systems. Non electric infusions systems are generally controlled by certain small diameter tubing (rate set) that regulates the flow. This method presents limitations including inability to change flow rate without changing the rate set, incorrect flow rate labeling due to the varying viscosities of fluids administered, and undesired flow rates due to device design limitations, patient conditions and environmental factors.

The flow rate control devices described hereinabove can be used in connection with gravity infusion devices and/or pressurized infusion devices, including constant or semi-constant force infusion devices. Additionally, if desired, a pressure sensor may be provided the output of which can be used to by self-adjusting mechanism or circuit to automatically adjust the flow rate of the flow rate device to reduce flow changes relative to pressure variations, patient conditions and other therapy factors.

The present disclosure is provided to allow practice of the invention, after the expiration of any patent granted hereon, by those skilled in the art without undue experimentation, and includes the best mode presently contemplated and the presently preferred embodiment. Nothing in this disclosure is to be taken to limit the scope of the invention, which is susceptible to numerous alterations, equivalents and substitutions without departing from the scope and spirit of the invention.

What is claimed is:

1. A variable flow rate infusion system, comprising:
   an infusion device that dispenses fluid pressurized to between 5 PSI and 40 PSI; and
   a manually-adjustable flow control device in fluid communication with the infusion device by way of tubing and configured to receive fluid dispensed by the infusion device, the flow control device comprising:
   a circular inlet handle including an inlet port, the inlet port being positioned offset a first distance from a center of the inlet handle;
   a circular outlet handle including an outlet port, the outlet port being positioned offset a second distance from a center of the outlet handle, the first distance being smaller than the second distance; and
   a seal sealingly engaged between the inlet handle and the outlet handle;
   wherein:
      manual rotation of at least a portion of the inlet handle relative to the outlet handle changes a width of a fluid path in the outlet handle which results in a change of a rate of fluid flow passing through the flow control device.

2. The variable flow rate infusion system of claim 1, wherein at least one of the inlet handle, outlet handle or seal includes a plurality of differently sized orifices and the manual rotation aligns one or more of the plurality of differently sized orifices between the inlet port and the outlet port.

3. The variable flow rate infusion system of claim 2, wherein the seal includes the plurality of differently sized orifices and rotation of a dial on the inlet handle rotates the seal to change the alignment of the plurality of differently sized orifices relative to the inlet port and outlet port.

4. The variable flow rate infusion system of claim 2, wherein the outlet handle includes the plurality of differently sized orifices in fluid communication with the outlet port, and rotation of the inlet handle changes the alignment of the inlet port and an orifice through the seal with the plurality of differently sized orifices.

5. The variable flow rate infusion system of claim 2, wherein each one of the plurality of differently sized orifices is differently sized from every other one of the plurality of differently sized orifices.

6. The variable flow rate infusion system of claim 2, wherein the plurality of differently sized orifices are arranged in groups representing different specific binary numbers and rotation of the portion of the inlet handle relative to the outlet handle selectively aligns a group of the plurality of differently sized orifices between the inlet port and the outlet port.

7. The variable flow rate infusion system of claim 1 further comprising:
   a catheter fluidically downstream from the flow control device to receive the fluid dispensed by the infusion device at a pressure lower than a fluid pressure output by the infusion device.

8. The variable flow rate infusion system of claim 1, wherein:
   the seal comprises at least one projection extending from an outer circumference; and
   the inlet handle comprises a cavity with at least one mating recesses configured to fit with the at least one projection to prevent the seal from moving within the cavity.

9. A variable flow rate infusion system, comprising:
   an infusion device that dispenses fluid pressurized to between 5 PSI and 40 PSI; and
   a manually-adjustable flow control device in fluid communication with the infusion device by way of tubing and configured to receive fluid dispensed by the infusion device, the flow control device comprising:
   a circular inlet handle including an inlet port, the inlet port being positioned offset a first distance from a center of the inlet handle;
   a circular outlet handle including an outlet port, the outlet port being positioned offset a second distance from a center of the outlet handle, the first distance being smaller than the second distance; and
   sealing means between the inlet handle and the outlet handle for changing a rate of fluid flow passing through the flow control device.

10. The variable flow rate infusion system of claim 9, wherein at least one of the inlet handle, outlet handle or sealing means includes a plurality of differently sized orifices and the manual rotation aligns one or more of the plurality of differently sized orifices between the inlet port and the outlet port.

11. The variable flow rate infusion system of claim 10, wherein the sealing means includes the plurality of differently sized orifices and rotation of a dial on the inlet handle rotates the sealing means to change the alignment of the plurality of differently sized orifices relative to the inlet port and outlet port.

12. The variable flow rate infusion system of claim 10, wherein the outlet handle includes the plurality of differently sized orifices in fluid communication with the outlet port, and rotation of the inlet handle changes the alignment of the inlet port and an orifice through the sealing means with the plurality of differently sized orifices.

13. The variable flow rate infusion system of claim 10, wherein each one of the plurality of differently sized orifices is differently sized from every other one of the plurality of differently sized orifices.

14. The variable flow rate infusion system of claim 10, wherein the plurality of differently sized orifices are arranged in groups representing different specific binary numbers and rotation of the portion of the inlet handle relative to the outlet handle selectively aligns a group of the plurality of differently sized orifices between the inlet port and the outlet port.

15. The variable flow rate infusion system of claim 9 further comprising:
   a catheter fluidically downstream from the flow control device to receive the fluid dispensed by the infusion device at a pressure lower than a fluid pressure output by the infusion device.

16. The variable flow rate infusion system of claim 9, wherein:

the sealing means comprises at least one projection extending from an outer circumference; and the inlet handle comprises a cavity with at least one mating recesses configured to fit with the at least one projection to prevent the sealing means from moving within the cavity.

17. A variable flow rate infusion system, comprising:

infusion means for dispensing pressurized fluid; and flow control means in fluid communication with the infusion means comprising:

a circular inlet handle including an inlet port, the inlet port being positioned offset a first distance from a center of the inlet handle;

a circular outlet handle including an outlet port, the outlet port being positioned offset a second distance from a center of the outlet handle, the first distance being smaller than the second distance; and     a seal sealingly engaged between the inlet handle and the outlet handle;

wherein:

rotation of at least a portion of the inlet handle relative to the outlet handle changes a width of a fluid path in the outlet handle which results in a change of a rate of fluid flow passing through the flow control means.

18. The variable flow rate infusion system of claim 17, wherein the flow control means dispenses the pressurized fluid at a pressure between 5 PSI and 40 PSI.

* * * * *